United States Patent
Genger et al.

(10) Patent No.: US 7,080,645 B2
(45) Date of Patent: Jul. 25, 2006

(54) ANTI-SNORING DEVICE, METHOD FOR REDUCING SNORING, AND A NASAL AIR CANNULA

(75) Inventors: Harald Genger, Dessau (DE); Martin Baecke, Dessau (DE); Hartmut Schneider, Lutherville, MD (US)

(73) Assignee: Seleon GmbH, Freiburg (DE)

( * ) Notice: Subject to any disclaimer, the term of this patent is extended or adjusted under 35 U.S.C. 154(b) by 0 days.

(21) Appl. No.: 10/623,779

(22) Filed: Jul. 21, 2003

(65) Prior Publication Data

US 2004/0016432 A1 Jan. 29, 2004

Related U.S. Application Data

(63) Continuation of application No. PCT/DE02/00422, filed on Feb. 5, 2002.

(51) Int. Cl.
*A61M 16/00* (2006.01)

(52) U.S. Cl. .............................. 128/204.18; 128/207.18
(58) Field of Classification Search ........... 128/203.17, 128/204.18, 204.24, 204.25, 205.26, 206.11, 128/207.18
See application file for complete search history.

(56) References Cited

U.S. PATENT DOCUMENTS

| | | | | |
|---|---|---|---|---|
| 50,641 A * | 10/1865 | Stone et al. | ................. | 454/238 |
| 718,785 A * | 1/1903 | McNary | ................... | 128/207.18 |
| 853,439 A * | 5/1907 | Clark | ................... | 128/207.18 |
| 859,156 A * | 7/1907 | Warnken | ................... | 454/238 |
| 909,002 A * | 1/1909 | Lambert | ................. | 128/204.15 |
| 1,125,542 A * | 1/1915 | Humphries | ............. | 128/207.18 |
| 1,129,619 A * | 2/1915 | Zapf | ...................... | 128/204.15 |
| 1,331,297 A * | 2/1920 | Walker | ................... | 128/207.18 |
| 2,693,800 A * | 11/1954 | Caldwell | ............... | 128/207.18 |
| 2,735,432 A * | 2/1956 | Hudson | ................. | 128/207.18 |
| 2,931,358 A * | 4/1960 | Sheridan | ................ | 128/207.18 |
| 3,172,407 A * | 3/1965 | Von Pechmann | ...... | 128/207.18 |
| 3,513,844 A * | 5/1970 | Smith | .................... | 128/207.18 |
| 3,643,660 A * | 2/1972 | Hudson et al. | ........ | 128/207.18 |
| 3,726,275 A * | 4/1973 | Jackson et al. | ........ | 128/207.18 |
| 3,802,431 A * | 4/1974 | Farr | ....................... | 128/207.18 |
| 3,881,480 A * | 5/1975 | Lafourcade | ............ | 128/200.21 |
| 3,985,131 A * | 10/1976 | Buck et al. | ............ | 128/204.23 |
| 4,106,505 A * | 8/1978 | Salter et al. | ........... | 128/207.18 |
| 4,266,540 A * | 5/1981 | Panzik et al. | .......... | 128/207.13 |
| 4,278,082 A * | 7/1981 | Blackmer | .............. | 128/207.18 |
| 4,462,398 A * | 7/1984 | Durkan et al. | ......... | 128/200.14 |
| 4,621,632 A * | 11/1986 | Bartels et al. | ......... | 128/203.27 |
| 4,915,105 A * | 4/1990 | Lee | .......................... | 128/205.27 |
| 4,989,599 A * | 2/1991 | Carter | ................... | 128/207.18 |
| 5,134,995 A * | 8/1992 | Gruenke et al. | ....... | 128/204.23 |
| 5,193,532 A * | 3/1993 | Moa et al. | ............ | 128/204.25 |
| 5,335,656 A * | 8/1994 | Bowe et al. | ........... | 128/207.18 |
| 5,349,946 A * | 9/1994 | McComb | ................ | 128/203.17 |
| 5,490,502 A * | 2/1996 | Rapoport et al. | ...... | 128/204.23 |
| 5,529,060 A * | 6/1996 | Salmon et al. | ......... | 128/203.16 |
| 5,537,997 A * | 7/1996 | Mechlenburg et al. | . | 128/204.23 |
| 5,682,878 A * | 11/1997 | Ogden | ................... | 128/204.23 |
| 5,687,715 A * | 11/1997 | Landis et al. | .......... | 128/207.18 |

(Continued)

*Primary Examiner*—Aaron J. Lewis
(74) *Attorney, Agent, or Firm*—Aliki K. Collins; AKC Patents LLC

(57) ABSTRACT

The application relates to an anti-snoring device comprising a compressor and a nasal air cannula, the air compressed by the compressor being blown through the nasal air cannula into the nose of a sleeping person. The invention also relates to an optimized nasal air cannula for the anti-snoring device.

16 Claims, 3 Drawing Sheets

U.S. PATENT DOCUMENTS

| | | | |
|---|---|---|---|
| 5,711,296 A * | 1/1998 | Kolobow | 128/205.13 |
| 5,975,077 A * | 11/1999 | Hofstetter et al. | 128/204.24 |
| 6,050,260 A * | 4/2000 | Daniell et al. | 128/204.22 |
| 6,561,188 B1 * | 5/2003 | Ellis | 128/206.11 |
| 6,591,834 B1 * | 7/2003 | Colla et al. | 128/204.21 |
| 6,595,215 B1 * | 7/2003 | Wood | 128/207.18 |
| 6,629,527 B1 * | 10/2003 | Estes et al. | 128/204.18 |
| 6,679,265 B1 * | 1/2004 | Strickland et al. | 128/207.18 |
| 6,705,315 B1 * | 3/2004 | Sullivan et al. | 128/204.18 |
| 6,745,768 B1 * | 6/2004 | Colla et al. | 128/204.21 |
| 6,769,432 B1 * | 8/2004 | Keifer | 128/206.11 |
| 6,776,163 B1 * | 8/2004 | Dougill et al. | 128/207.18 |

* cited by examiner

ANTI-SNORING DEVICE, METHOD FOR REDUCING SNORING, AND A NASAL AIR CANNULA

CROSS REFERENCE TO RELATED CO-PENDING APPLICATIONS

This application is a continuation of international application number PCT/DE 02/00422 (Publication number WO 02/062413) filed on Feb. 5, 2002 and entitled ANTI-SNORING DEVICE, METHOD FOR REDUCING SNORING AND AIR GLASSES and claims the benefit of the above mentioned PCT application and the corresponding German National application Serial No. 10105383.5 filed on Feb. 6, 2001 and entitled ANTISCHNARCHGERAET, VERFARREN ZUR VERRINGERUNG DES SCHNARCHENS SOWIE LUFTBRILLE which are commonly assigned and the contents of which are expressly incorporated herein by reference.

FIELD OF THE INVENTION

The present invention relates to an economical device and to a method for reducing snoring and to a nasal air cannula.

More specifically, the invention provides devices and a method for administering a positive airway pressure therapy.

BACKGROUND OF THE INVENTION

Obstructive respiratory disorders entail apnea (respiratory arrest) causing the sleeping person to wake up. Frequent apnea prevents the sleeping sufferer from entering recuperative deep sleep. As a result, sufferers incurring apnea during their sleep are sleep-deprived during the day: social problems may arise at work and in the worst case fatal accidents may be incurred, for instance as regards professional truck drivers.

Devices for carrying out the therapy of Continuous Positive Airway Pressure (CPAP) are known in the state of the art. CPAP therapy is described in detail in CHEST, vol. 110, pp 1077 through 1088, October 1996 and in SLEEP, vol. 19, pp 184 through 188.

In CPAP therapy, a constant, excess pressure is fed to a patient through a nasal mask. When the excess pressure is properly selected, it keeps the upper airway fully open overnight and as a result obstructive respiratory disorders do not arise. In part the required pressure depends on the sufferer's sleep stage and his/her body position. A therapeutic device (AutoCPAP) is known from the German patent document 198 49 571 A1 which automatically adjusts the applied pressure and thus matches it to the sleep stage and the body position.

Moreover nasal oxygen cannulae for oxygen treatment are known in the state of the art. Using the nasal oxygen cannula, air containing a higher partial oxygen pressure (>210 mbars) or pure oxygen is administered into the nose. Illustratively oxygen treatment is applied for acute or chronic hypoxemia caused by respiratory or cardiac circulatory disorders (mycroinfarct, shock) or certain poisonings, for instance by carbon monoxide, carbon dioxide, coal gas or smoke.

Lastly it is known treating race horses following racing with moistened air. The moistened air is introduced into the horse's nostrils by a device similar to a nasal oxygen cannula but matched to the shape of the horse's head. Because of the high volume of breathing when running, the horse's nasal mucous membrane is unable to deliver enough moisture, and consequently the nasal mucous membrane dries up.

SUMMARY OF THE INVENTION

The objective of the present invention is a device which is both economical and comfortable and also a method reducing snoring and a nasal air cannula.

The objective is attained by means of an anti-snoring device defined in claim 1, a method defined in claim 13 and a nasal air cannula defined in claim 15.

As regards sufferers who do snore but are free of pathological apnea, claim 1 advantageously offers an anti-snoring device which requires less flow than devices used in CPAP therapy and with which accordingly a smaller compressor may be used. Moreover, when compared with the conventional masks used in CPAP therapy, the nasal air cannula offers higher wearing comfort and higher safety because normal breathing through the nose in the event of compressor turbine failure shall nevertheless take place on account the nose being only partly closed.

An air humidifier precludes the nasal mucous membrane of the sleeping person from drying out and in this manner raises the comfort level. In order not to disturb the companion of the sleeping person by compressor noise superceding the snoring noise, said compressor is optimized acoustically. In order to further reduce compressor noise, the anti-snoring device is fitted with a long conduit allowing moving the compressor into an adjacent room.

The flow of air may be advantageously controlled in three ways: by means of the angular turbine speed, by means of a throttling valve and/or by means of a bypass valve. Controlling the angular turbine speed offers the advantage of low noise at low angular speed and a slight pressure differential. Accordingly controlling the flow of air by means of the angular turbine speed when the throttling valve is closed or absent and while the bypass valve is absent, the least generation of compressor noise is attained. On the other hand if the compressor is mounted in an adjacent room, then only a throttling valve or a bypass valve are the economically applicable ways to control the flow of air in the vicinity of the sleeping person. The advantage offered by a throttling valve is that it reduces the flow of air through the compressor and hence its power drain. Non-adjustable bypass valves are known in CPAP therapy. They are required in this field to allow the patient to exhale in spite of applied face mask.

Using a conduit of slight inside diameter and slight outer diameter preferably 4 and 6 mm respectively offers the advantage extended, repeated use and hence the economy of such tubing.

A conduit segment of substantial inside diameter offers the advantage of little pressure drop.

Advantageously an air humidifier situated near the sleeping person allows adjusting the water-bath temperature from the bed and to replenish the water from this bed. Contrary to using a compressor, an air humidifier does not generate operational noises and therefore its configuration near the bed is problem-free.

Integrating a compressor and an air humidifier in one apparatus offers the advantage of low prices.

A nasal air cannula substantially well sealed against the nose of the sleeping person offers the advantage that the bypass' air resistance does not depend on the residual gap between nose and a nasal air cannula but instead can be accurately adjusted by means of the defined size of the apertures in the nasal air cannula.

Advantageously, a nasal air cannula fitted with preferably two jacket pipes requires less of an air flow and accordingly the pressure drop in the feed tubing shall be less. Advantageously again, using an jacket pipe does not require sealing the patient's nostrils, instead a defined cross-section shall remain open, so that, even if the compressor should fail, the patient still shall be able to inhale and exhale through the jacket pipe.

Advantageously a design of constriction and diffusor reinforces a jet pump effect.

Advantageously a measuring tubule 26 is used, allowing measuring the pressure generated by the nasal air cannula in the patient's airways. Such measurement makes it possible detecting the patient's inhaling and exhaling and to raise the air flow through the nozzle and hence increasing the pressure generated by the nasal air cannula in the patient's when said patient is inhaling and to lower said pressure again when said patient is exhaling.

BRIEF DESCRIPTION OF THE DRAWINGS

Preferred embodiments of the present invention are elucidated below in relation to the appended drawings.

DETAILED DESCRIPTION OF THE INVENTION

Snoring is generated during sleep by impulsive oscillation of the slackly hanging soft palate when, on account of loss of tone in the jaw and tongue muscles, the lower jaw has sunk straight down and the tongue has dropped rearward. This phenomenon is termed obstructive snoring. Snoring also may be produced by habit (common snoring).

The objectives of the present invention apply to snoring persons who however do not suffer from pathological apneas.

Figure 1:
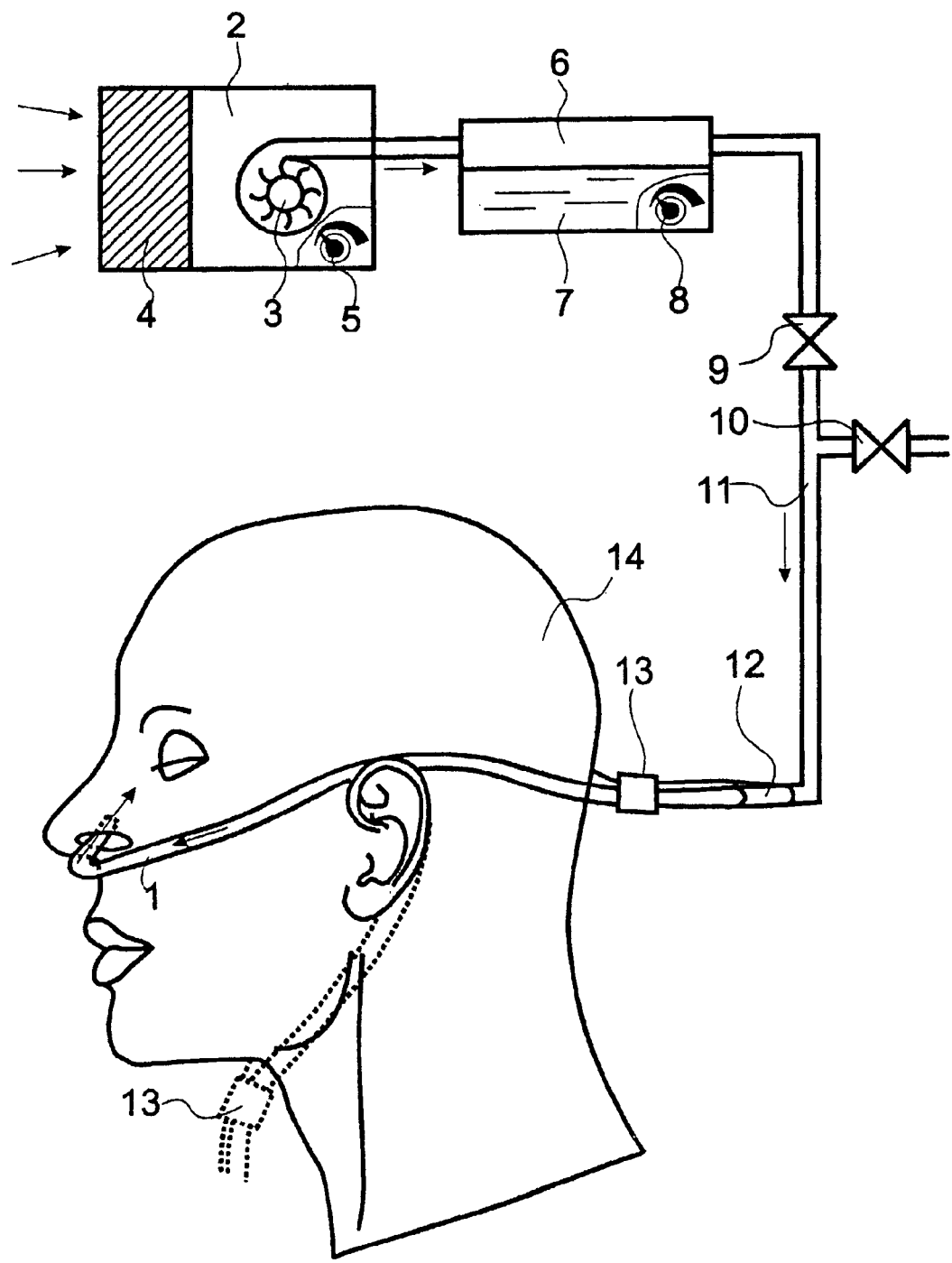
FIG. 1 is a side view toward the snorer's head of the anti-snoring device of the present invention.
Figure 2:
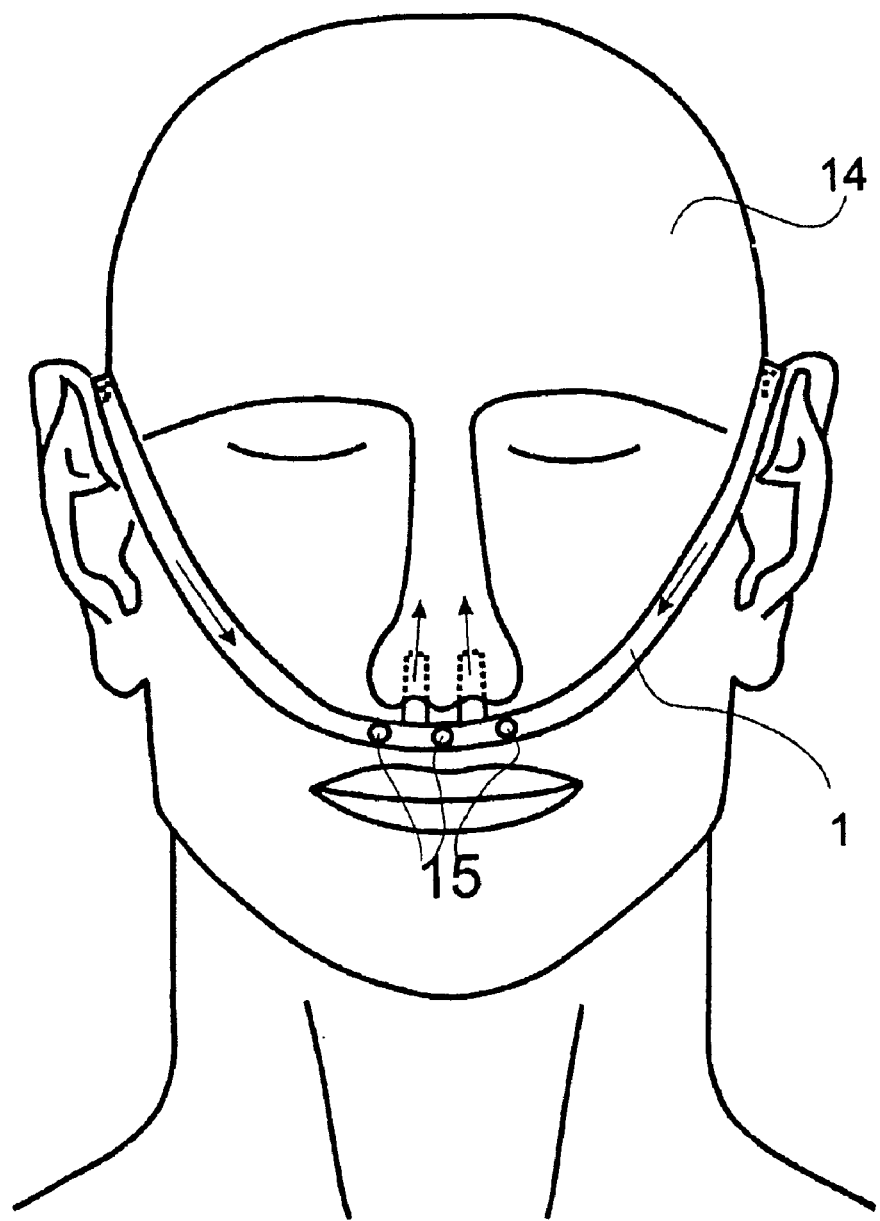
FIG. 2 is a front view of the sleeping person's face fitted with a nasal air cannula.

FIG. 1 shows a sleeping person 14 nasally receiving air through a nasal air cannula 1. This applied air assures a slightly higher air pressure of 2 to 20 mbars in the sleeping person's airways. This slight excess of pressure widens the airways. Consequently the sagging down of the lower jaw and the rearward lowering of the tongue are counteracted.

Basically the nasal air cannula consists of two tubes running rearward on the ears. Both tubes are joined at a Y-arm into one tube 12. A displaceable ring 13 matches the nasal air cannula to the sleeping person's head size. Alternatively to the support configuration shown in FIG. 1, the two tubes may run, not on the ears and rearward, but around the ears and then being joined below the lower jaw as indicated in dashed lines in FIG. 1.

In typical nasal air cannulae, the conduit 11 between the compressor 2 or air humidifier 6 and the junction 12 exhibits an inside diameter less than 10 mm, for instance 4 mm, and an outside diameter less than 12 mm, for instance 6 mm. The tube segments between the patient's nose and the Y junction 12 illustratively exhibit an inside diameter also less than 10 mm, for instance 3 mm, and an outside diameter less than 12 mm, for instance 5 mm. Because of these small cross-sections, the pressure drop in the tubes is significant.

Accordingly the compressor 2 should be able to generate excess pressure from 100 to 1,000 mbars relative to the ambient pressure. The larger the selected diameters of the tube segments, the lower may be the compressor output pressure.

In the conventional manner regarding nasal oxygen cannulae, the nasal air cannula' outlets may be smaller than the nostril apertures of the sleeping person. In this case the sleeping person is able to exhale through the gap between the outlets and the nasal cannulae. So to speak, said gap subtends a non-adjustable bypass.

On the other hand the nasal air cannula' outlets may be matched to the shape of the nostrils with which they then form a substantially tight seal. In this case apertures 15 may be present in the nasal air cannula for purposes of exhalation, and these apertures may be completed by displaceable or rotatable elements to constitute an adjustable valve.

The compressed air is generated by a compressor 2. To obviate replacing snoring noise by other unpleasant noises, the compressor 2 is optimized acoustically. It is also fitted with acoustic insulation 4. A turbine regulator 5 is provided In order that the compressor turbine 3 run at the lowest possible angular speed. In this manner not only is the noise generated by the turbine minimized, but also the power drain by the compressor.

In a preferred embodiment of the present invention, the air compressed by the compressor first is made to pass through an air humidifier 6 before it is fed to the nasal air cannula. The air is made to pass over a water bath 7 in the air humidifier. The water bath temperature may be set by a temperature control 8. The higher the water bath temperature, the more the air shall be humidified in the air humidifier.

In addition or alternatively to the turbine regulator 5, the conduit 11 also may be fitted with a throttling valve 9 and/or a bypass valve 10 to control the flow of air. Preferably both valves shall be configured near the sleeping person who shall then be able to control the air flow from his/her bed, even when the compressor is located in the adjacent room and thus the sleeping person cannot from his/her bed operate the turbine regulator.

If the compressor 2 is located in the next room and the air humidifier 6 is next to the sleeping person's bed, then the conduit segment between the compressor 2 and the air humidifier 6 preferably shall exhibit an inside diameter of 10 to 20 mm for the purpose of minimizing the pressure drop across this conduit segment.

When the nasal air cannula does not substantially form a tight seal with the sleeping person's nostrils, flow regulation shall be preferably implemented using a throttling valve 9 rather than a bypass valve.10. On one hand the throttling valve does not entail an additional airflow and on the other hand the leakage between the nasal air cannula and the nose acts as a bypass permitting the sleeping person to exhale. If on the other hand the nasal air cannula substantially seals off the sleeping person's nostrils, a bypass will be required to allow the sleeping person to exhale.

In a further preferred embodiment of the present invention, the nasal air cannula may be a nasal oxygen cannula which is already commercially available. In still another preferred embodiment, the nasal air cannula may be replaced by a mask covering the nose and possibly also the mouth.

Figure 3:
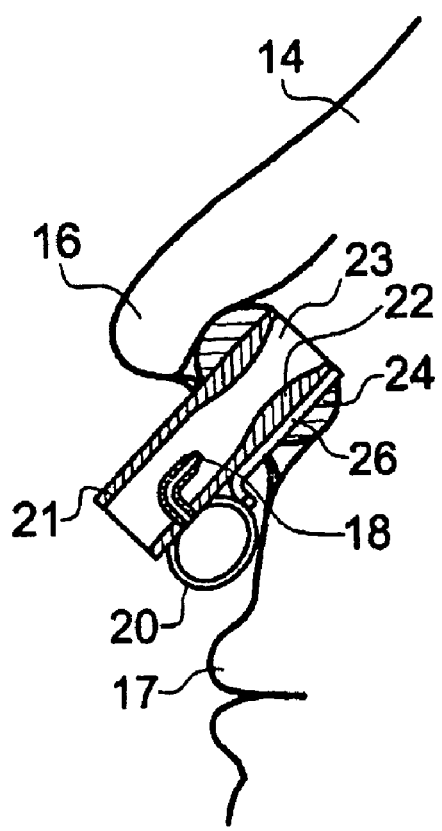
FIG. 3 is a cross-section of a nasal air cannula with jacket pipe.
Figure 4:
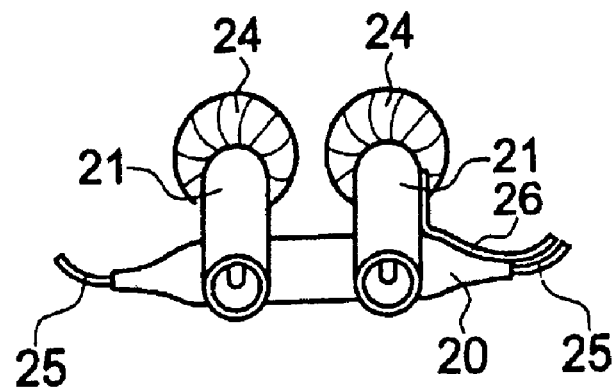
FIG. 4 shows nasal air cannulas fitted with two jacket pipes.

FIG. 3 is a cross-section of a special embodiment of a nasal air cannula. FIG. 4 shows this embodiment in perspective. These nasal air cannulae include feed lines 25, a dispenser 20, also a jacket pipe 21 for each nostril of a patient. At its end close to the patient's nose, each jacket pipe is fitted with an ergonomic pad 24 at its outer rim, said pad fully or substantially fully sealing the patient's nostril during operation. A nozzle 18 through which is blown pressurized air toward the nostril is mounted in each jacket pipe. The inside cross-section of the jacket pipe comprises a constriction 22 between the nozzle 18 and said jacket pipe's end near the patient's nose. That zone between the constriction 22 and the jacket pipe's end near the patient's nose wherein the inside diameter of the jacket pipe flares toward the said jacket pipe's end close to the patient's nose is called "diffusor" 23. Moreover either or both jacket pipes may be fitted with a measuring tubule 26 by means of which the pressure inside the patient's nose may be measured.

The inside of the jacket pipe 21 cooperates with the nozzle 18 in the manner of a jet pump. By means of the nozzle, a small flow of air enters the jacket pipe and in this way pumps additional air through the jacket pipe's end into the patient's nose. In other words, the nozzle 18 and jacket pipe 21 jointly transform a small flow of air generated by a higher excess pressure into a larger flow of air at a lesser excess pressure. The particular advantage of this feature in particular is that only part of the flow of air from the compressor 2 into the nose need be fed to the nozzle 18. Because of the lesser flow of air, the pressure drop in the conduit 11 is less. If on the other hand a constant pressure drop is acceptable, then the cross-section of the conduit 11 may be selected to be smaller when using the nasal air cannula shown in FIGS. 3 and 4.

As already mentioned above, the compressor 2 must be able to generate 100 to 1,000 mbar excess pressure relative to the ambient pressure. In particular the outer contour of the ergonomic pads, but also the jacket pipe, are matched to the patient's nasal geometry. The jacket pipe may be circular and exhibit a diameter of 4 to 12 mm. In other embodiments the jacket pipe may be cross-sectionally elliptical, the smaller and the larger radii illustratively being in the range of 2 to 6 mm. The jacket pipe may be 20 to 50 mm, in particular it may be 30 mm long. The conduit 11 is 1 to 2 m long. Other sizes are determined by the corresponding body parts of the patients.

So-called Bi-PAP devices have been developed to make the patient more comfortable. These devices support patient's inhaling and exhaling in that the compressor applies a higher pressure during inhaling than exhaling. The German patent applications 101 18 968.0 and 102 00 183.9 describe the manner of detecting inhaling and exhaling. The latter application moreover relates to compensating the pressure drop in an artificial respiration conduit 11 to make the patient more comfortable.

In the light of present knowledge, the relatively minor pressure fluctuations in the nose and the jacket pipes generated by the patient's inhaling and exhaling do not materially affect the high excess pressure typically of 100 to 1,000 mbars in the conduit 11, and consequently such fluctuations will elude detection by economical test equipment in the conduit 11 or preferably at the output of the turbine 3 in the compressor 2. As a result a measuring tubule 26 may be used allowing measuring the pressure inside the nose and hence in the patient's airways. The measuring tubule 26 may run parallel to the conduit 11 to the compressor housing which is fitted with a pressure sensor. In other embodiments the pressure sensor measuring the inside nasal pressure may be mounted outside the housing of the compressor 2, for instance near the Y junction 12. The measuring tubule 26 may be configured at only one of the two jacket pipes. In another embodiment it may be fork-shaped whereby one end of the measuring tubule is situated in each jacket pipe end. The nasal air cannula embodiment shown in FIG. 4 configures symmetrically two feed lines 25 to the nozzles 18 in the two jacket pipes. The measuring tubule 26 runs back to one of the two feed lines. In another embodiment merely one feed line 25 is present and the measuring tubule 26 runs back on the other side. As regards the latter embodiment, the feed line 25 running parallel measuring tubule 26 no longer exists. The measuring tubule 26 and the other feed line assure that the jacket pipes are mechanically affixed in the patient's nose.

The present invention has been elucidated above by means of preferred embodiments. However it is obvious to the expert that diverse alterations and modifications may be introduced without thereby deviating from the spirit of the invention. Accordingly the scope of protection is determined by the claims below and their equivalents.

| | |
|---|---|
| 1 | nasal air cannula |
| 2 | compressor |
| 3 | turbine |
| 4 | acoustic insulation |
| 5 | turbine control means |
| 6 | air humidifier |
| 7 | water bath |
| 8 | temperature control |
| 9 | throttling valve |
| 10 | bypass valve |
| 11 | conduit |
| 12 | Y junction |
| 13 | ring |
| 14 | sleeping person |
| 15 | bypass apertures |
| 16 | sleeping person's nose |
| 17 | upper lip |
| 18 | nozzle |
| 19 | upper lip |
| 20 | dispenser |
| 21 | jacket pipe |
| 22 | constriction |
| 23 | diffusor |
| 24 | ergonomic pad |
| 25 | feed lines |
| 26 | measuring tubule |

What is claimed is:

1. A method of reducing snoring during sleeping comprising:
   providing a compressor and a tube connected to said compressor;
   providing a snore-reducing nasal air cannula connected to said tube;
   attaching said snore-reducing nasal air cannula to a sleeping person's nose;
   feeding compressed air from said compressor through said tube to said snore-reducing air cannula and thereby to said sleeping person's nose; and
   wherein said snore-reducing cannula comprises an outlet said outlet having a jacket pipe, wherein said jacket pipe has an end near said sleeping person's nose and said end is configured so that during operation it seals substantially tightly said sleeping person's nose, and wherein a nozzle is configured in the jacket pipe, said nozzle allowing blowing air toward said end of the jacket pipe near said sleeping person's nose and wherein said jacket pipe further comprises an inside wall having a narrowing between said nozzle and said end near said sleeping person's nose and then flaring out from said narrowing toward said end near said sleeping person's nose and thereby forming a diffusor.

2. The method of claim 1, further comprising providing an air humidifier and passing said compressed air through said air humidifier before feeding said compressed air to said sleeping person's nose.

3. An anti-snoring device comprising a compressor and a tube connected to said compressor, wherein said compressor feeds compressed air through said tube to a snore-reducing nasal air cannula and said snore-reducing nasal air cannula in turn applies said compressed air into a sleeping person's nose and wherein said snore-reducing nasal air cannula comprises,
 an outlet said outlet having a jacket pipe, wherein said jacket pipe has an end near said sleeping person's nose and said end is configured so that during operation it seals substantially tightly said sleeping person's nose, and wherein a nozzle is configured in the jacket pipe, said nozzle allowing blowing air toward said end of the jacket pipe near said sleeping person's nose and wherein said jacket pipe further comprises an inside wall having a narrowing between said nozzle and said end near said sleeping person's nose and then flaring out from said narrowing toward said end near said sleeping person's nose and thereby forming a diffusor.

4. The anti-snoring device as claimed in claim 3, wherein said compressed air is fed through an air humidifier before reaching said snore-reducing nasal air cannula.

5. The anti-snoring device as claimed in claim 4, wherein the air humidifier comprises a water bath and a temperature control controlling the temperature of the water bath and hence the degree of air humidification.

6. The anti-snoring device as claimed in claim 4, wherein said tube comprises a segment of substantial length exhibiting a widened diameter of 10 to 20 mm.

7. The anti-snoring device as claimed in claim 4, wherein said tube is long enough so that the compressor may be located not in a bedroom where said sleeping person sleeps bat in an adjacent room and wherein said air humidifier is configured in the vicinity of the sleeping person.

8. The anti-snoring device as claimed in claim 4, wherein the compressor and the air humidifier are integrated into one apparatus.

9. The anti-snoring device as claimed in claim 3, wherein said tube is long enough so that the compressor may be located not in a bedroom where said sleeping person sleeps but in an adjacent room.

10. The anti-snoring device as claimed in claim 3, wherein said compressor comprises a control controlling an angular speed of a turbine of said compressor, thereby controlling flow of air through the nasal air cannula.

11. The anti-snoring device as claimed in claim 3, wherein said tube comprises a throttling valve controlling pressure drop across said tube and thereby flow of air through the tube.

12. The anti-snoring device as claimed in claim 3, further comprising a bypass valve running from the tube into ambient in such manner that flow of air through the snore-reducing nasal air cannula is controlled by said bypass valve.

13. The anti-snoring device as claimed in claim 3, wherein said tube comprises an inside diameter of less than 10 mm.

14. The anti-snoring device as claimed in claim 3, wherein said tube comprises an inside diameter of 4 mm and an outside diameter of 6 mm.

15. A snore-reducing nasal air cannula comprising,
 an outlet said outlet having a jacket pipe, wherein said jacket pipe has an end near a patients' nose and said end is configured so that during operation it seals substantially tightly the patient's nose, and wherein a nozzle is configured in the jacket pipe, said nozzle allowing blowing air toward said end of the jacket pipe near the patient's nose and, wherein said jacket pipe further comprises an inside wall having a narrowing between said nozzle and said end near the person's nose and then flaring out from said narrowing toward said end near the person's nose and thereby forming a diffusor.

16. The nasal air cannula as claimed in claim 15, further comprising a measuring tubule fitted with an aperture in the vicinity of said end near the patient's nose, said measuring tubule allowing measuring pressure in the nose of the patient.

\* \* \* \* \*